United States Patent [19]

Weber et al.

[11] Patent Number: 5,516,649

[45] Date of Patent: May 14, 1996

[54] PROCESS FOR THE PRODUCTION OF 4-ANDROSTENE-3,17-DIONE AND 1,4-ANDROSTADIENE-3,17-DIONE FROM ERGOSTEROL WITH MYCOBACTERIUM

[75] Inventors: Alfred Weber; Mario Kennecke, both of Berlin, Germany

[73] Assignee: Schering Aktiengesellschaft, Berlin, Germany

[21] Appl. No.: 266,442

[22] Filed: Jun. 28, 1994

Related U.S. Application Data

[63] Continuation of Ser. No. 55,692, May 3, 1993, abandoned, which is a continuation of Ser. No. 604,305, Oct. 29, 1990, abandoned, which is a continuation of Ser. No. 29,505, filed as PCT/DE86/00228, Jun. 2, 1986, abandoned.

[30] Foreign Application Priority Data

Jun. 10, 1985 [DE] Germany .................. 35 21 111.3

[51] Int. Cl.$^6$ .................................................. C12P 33/16
[52] U.S. Cl. ........................... 435/55; 435/865; 435/863; 435/253.1; 435/253.2
[58] Field of Search ..................... 435/55, 865, 863, 435/253.1, 253.2

[56] References Cited

U.S. PATENT DOCUMENTS

| | | | |
|---|---|---|---|
| 3,684,657 | 8/1972 | Kraychy | 435/55 |
| 3,759,791 | 9/1973 | Marsheck | 435/55 |
| 4,293,645 | 10/1981 | Wovcha et al. | 435/55 |

FOREIGN PATENT DOCUMENTS

| | | | |
|---|---|---|---|
| 57-152898 | 9/1982 | Japan . | |
| 7152898 | 9/1982 | Japan | 435/55 |

OTHER PUBLICATIONS

Pavia et al, "Introduction to Organic Laboratory Techniques", 1976, pp. 14–15.
Ambrus et al., *Experentia*, vol. 24, p. 432, 1968.
Wix et al., *Steroids*, vol. 11, pp. 401–413, 1968.
Nagasawa et al., Agr. Biol. Chem., vol. 34, No. 5, pp. 798–800, 1970.
Goodfellow et al., The Biol of the Actinomycetes, pp. 40–44, 74–75, 1986.
Marsheck et al., Applied Micro. Jan. 1972, pp. 72–77.
Goodfellow et al, *The Biology of the Actinomycetes,* 1984, Academic Press.

Primary Examiner—Irene Marx
Attorney, Agent, or Firm—Millen, White, Zelano & Branigan

[57] ABSTRACT

A process for the production of 4-androstene-3,17-dione and 1,4-androstadiene-3,17-dione of the general formula

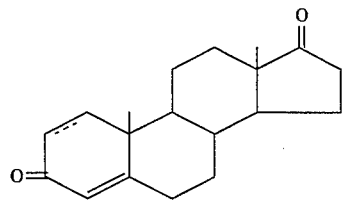

wherein . . . . . symbolizes a single bond or a double bond, characterized in that ergosterol

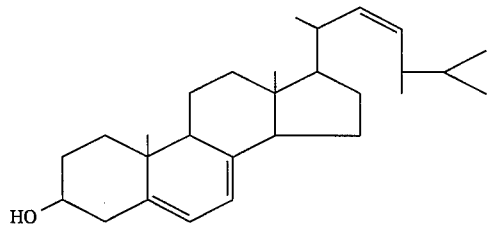

is fermented with a culture of a microorganism strain capable of side-chain degradation of sterols.

6 Claims, No Drawings

PROCESS FOR THE PRODUCTION OF 4-ANDROSTENE-3,17-DIONE AND 1,4-ANDROSTADIENE-3,17-DIONE FROM ERGOSTEROL WITH MYCOBACTERIUM

CROSS-REFERENCE TO RELATED APPLICATIONS

This application is a continuation of U.S. patent application Ser. No. 08/055,692, was abandoned, filed May 3, 1993, which is a continuation of Ser. No. 07/604,305, filed Oct. 29, 1990 now abandoned, which is a continuation of U.S. application Ser. No. 07/029,505, filed as PCT/DE86/00228, Jun. 2, 1986, now abandoned.

The invention relates to the process characterized in the claims.

It is known that numerous microorganisms (for example those of the genera Arthrobacter Brevibacterium MICROBACTERIUM PROTAMINOBACTER BACILLUS NORCARDIA, STREPTOMYCES and especially MYCOBACTERIUM) which have the natural capability of degrading naturally occurring 3betahydroxy-Δ5 sterols (such as cholesterol or sitosterol) to carbon dioxide and water and that during this degradation 4-androstene-3,17-dione and 1,4-androstadiene-3,17-dione are intermediately formed.

Further it is known that with the help of inhibitor additives or mutated microorganisms it is possible to direct the degradation of the sterols so that a degradation of the formed 4-androstene-3,17-dione or 1,4-androstadiene-3,17-dione is avoided (see German laid-open specifications 15 43 269 and 15 93 327 and also U.S. Pat. No. 3,684,657).

It is surprising for a man of the art that under known conditions the side chain of ergosterol is also degraded, since it is known that the side chain degradation of sterols is caused by a complex enzyme system and it could not be expected that all enzymes taking part in the side chain degradation of natural steroids have the capability of also causing the side chain degradation of this compound. Moreover, it could not be foreseen that with this degradation the Δ7 double bond of the ergosterol is hydrogenated.

Except for the use of other initial compounds, the process according to the invention is performed under the same fermentation conditions that are used in known microbiological side chain degradation reactions of sterols.

According to the invention the fermentation is performed by use of the microorganism culture which is usually used for side chain degradation of sterols. Suitable cultures are, for example, bacterial cultures capable of side chain degradation of sterols of the genera ARTHROBACTER, BREVIBACTERIUM, MICROBACTERIUM, PROTAMINOBACTER, STREPTOMYCES or especially the genus MYCOBACTERIUM. As suitable microorganisms there can be mentioned, for example: MICROBACTERIUM LACTUM IAM-1640, PROTAMINOBACTER ALBOFLAVUS IAM-1040, BACILLUS ROSEUS IAM-1257, BACILLUS SPHAERICUS ATTC-7055, NORCARDIA GARDNERI IAM-105, NORCARDIA MINIMA IAM-374, NORCARDIA CORALLINA IFO-3338, STREPTOMYCES RUBESCENS IAM-74 or especially the microorganisms MYCOBACTERIUM AVIUM IFO-3082, MYCOBACTERIUM PHLEI IFO-3158, MYCOBACTERIUM PHLEI (Institute for Health, Budapest No. 29), MYCOBACTERIUM PHLEI ATCC-354, MYCOBACTERIUM, SMEGMATIS IFO-3084, MYCOBACTERIUM SMEGMATIS ATCC-20, MYCOBACTERIUM SMEGMATIS (Institute for Health, Budapest No. 27). MYCOBACTERIUM SMEGMATIS ATCC-19979 and MYCOBACTERIUM FORTUITUM CBS-49566.

Especially preferred as microorganisms are MYCOBACTERIUM SPEC. NRRL B-3805, MYCOBACTERIUM SPEC. NRRL B-3683, MYCOBACTERIUM PHLEI NRRL B-8154 and MYCOBACTERIUM FORTUITUM NRRL 8-8153 with whose help ergosterol can be run without the use of additional inhibitors inhibiting the 9alpha hydroxylation.

Submerged cultures are incubated under the culture conditions usually used for the microorganisms in a suitable nutrient medium with aeration. Then the substrate (dissolved in a suitable solvent or preferably in emulsified form) is added to the cultures and fermented until a maximum substrate conversion is achieved.

Suitable substrate solvents are, for example, methanol, ethanol, glycol monomethyl ether, dimethylformamide or dimethylsulfoxide. Emulsification of the substrate can be produced, for example, by spraying it in micronized form or dissolved in a water-miscible solvent (such as methanol, ethanol, acetone, glycol monomethyl ether, dimethylformamide or dimethylsulfoxide) with strong turbulence in (preferably decalcified) water, which contains the usual emulsification auxiliary agents. Suitable emulsification auxiliary agents are nonionogenic emulsifiers such as, for example, ethylene oxyadducts or fatty acid esters of polyglycols. As suitable emulsifiers the commercial wetting agents Tegin(R), Tween(R) and Span(R) can be mentioned as examples.

The optimal substrate concentration, substrate addition time and fermentation period depend on the structure of the substrate used and the type of microorganism used. These amounts, as is generally necessary in microbiological steroid transformations, must be determined in each case by preliminary tests familiar to a man of the art.

The 4-androstene-3,17-dione derivatives of general formula I, which can be produced according to the process of the invention, as is known, are valuable intermediate products which today are used commercially for synthesis of pharmacologically effective steroids.

The following examples serve to explain the process according to the invention.

EXAMPLE 1

A 2-liter Erlenmeyer flask with 500 ml of sterile nutrient containing

1% yeast extract 0.45% disodium hydrogen phosphate 0.34% potassium dihydrogen phosphate and 0.2% Tween(R) 80 adjusted to pH 6.7 is inoculated with a suspension of a MYCOBACTERIUM SPEC. NRRL B-3805 dry culture and is shaken for 3 days at 30° C at 190 rpm.

20 Erlenmeyer flasks (500 ml) each with 100 ml of sterile nutrient containing 2.5% corn steep liquor 0.3% diammonium hydrogen phosphate 0.25% soybean flour and 0.25% Tween (R) 80 adjusted to pH 7.0 are inoculated with 5 ml in each case of MYCOBACTERIUM SPEC. incubation culture and shaken 24 hours at 30° C. at 220 rpm. Then 30 mg of ergosterol dissolved in 1.5 ml of dimethylformamide is added to each culture and fermented for another 96 hours at 30° C.

The combined cultures are extracted with ethylene chloride, the extract is concentrated in a vacuum, the residue is purified by chromatography over a silica gel column and, after recrystallization from diisopropyl ether, 150 mg of 4-androstene-3,17-dione is obtained.

In addition, 380 mg of unreacted ergosterol is recovered.

EXAMPLE 2

Under the conditions of example 1, but with MYCOBACTERIUM SPEC. NRRL B-3683 being used, 600 mg of ergosterol is reacted, prepared and, besides 400 mg of unreacted ergosterol, 130 mg of 1,4-androstadiene-3,17-dione is obtained.

I claim:

1. A process for the production of 4-androstene-3,17-dione of the formula

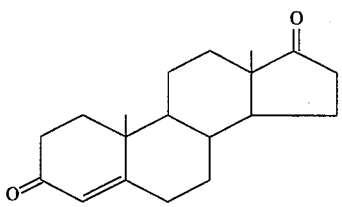

comprising:
  culturing Mycobacterium spec. NRRL B-3805 in the absence of a 9α-hydroxylation inhibitor;
  adding ergosterol to said cultured Mycobacterium, wherein said ergosterol is dissolved in a solvent selected from the group consisting of methanol, ethanol, glycol monomethyl ether, dimethylformamide, and dimethylsulfoxide;
  further culturing said strain in the absence of said inhibitor; and
  isolating the resultant 4-androstene-3,17-dione.

2. A process according to claim 1, wherein the solvent is dimethylformamide.

3. A process according to claim 1, wherein said Mycobacterium is cultured for about 24 hours prior to adding said ergosterol.

4. A process for the production of 1,4-androstadiene-3,17-dione of the formula

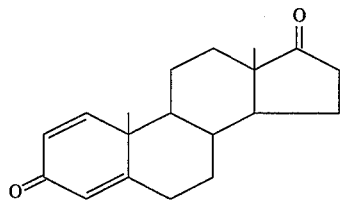

comprising:
  culturing Mycobacterium spec. NRRL B-3683 in the absence of a 9α-hydroxylation inhibitor;
  adding ergosterol to said cultured Mycobacterium, wherein said ergosterol is dissolved in a solvent selected from the group consisting of methanol, ethanol, glycol, monomethyl ether, dimethylformamide, and dimethylsulfoxide;
  further culturing said strain in the absence of said inhibitor; and
  isolating the resultant 1,4-androstadiene-3,17-dione.

5. A process according to claim 4, wherein the solvent is dimethylformamide.

6. A process according to claim 4, wherein said Mycobacterium is cultured for about 24 hours prior to adding said ergosterol.

* * * * *